United States Patent [19]

Solladie et al.

[11] Patent Number: 5,191,110
[45] Date of Patent: Mar. 2, 1993

[54] PROCESS FOR THE SYNTHESIS OF VITAMIN A AND CERTAIN ONES OF DERIVATIVES

[75] Inventors: Guy Solladie, Strasbourg; Serge Forestier, Claye-Souilly; Gérard Lang, Saint-Gratien, all of France

[73] Assignee: L'Oreal, Paris, France

[21] Appl. No.: 871,710

[22] Filed: Apr. 21, 1992

Related U.S. Application Data

[63] Continuation of Ser. No. 197,820, May 23, 1988, abandoned.

[51] Int. Cl.$^5$ ............................................. C07C 67/02
[52] U.S. Cl. .................................................. 560/260
[58] Field of Search ........................................ 560/260

[56] References Cited

U.S. PATENT DOCUMENTS 2,577,538  4/1951  Milas ................................... 560/260

OTHER PUBLICATIONS

J. Am. Chem. Soc., 1982, pp. 5807–5808, American Chemical Society, Walborsky et al.

Primary Examiner—Jose G. Dees
Assistant Examiner—Joseph M. Conrad
Attorney, Agent, or Firm—Cushman, Darby & Cushman

[57] ABSTRACT

According to this process, one effects a stereospecific reduction of the two hydroxyl groups of an ether-diol by a mixture (titanium trichloride, lithium aluminum hydride) at a temperature between 5° C. and about 40° C. and that optionally, one converts the resulting ether into vitamin A, retinol or retinoic acid.

Application to the synthesis of all-trans compounds selected from the group consisting of vitamin A and its ethers, retinol and retinoic acid, and their 13-cis isomers.

5 Claims, No Drawings

PROCESS FOR THE SYNTHESIS OF VITAMIN A AND CERTAIN ONES OF DERIVATIVES

This is a continuation of application Ser. No. 07/197,820, filed May 23, 1988, now abandoned.

The present invention relates to a synthesis process permitting to obtain, on the one hand, all-trans compounds selected from the group consisting of vitamin A and its ethers, retinol and retinoic acid, and, on the other hand, their 13-cis isomers.

In Japanese patent No. 3678/1964, there is described the reduction, by lithium aluminum hydride, in solution in ethyl ether, of a compound of the formula

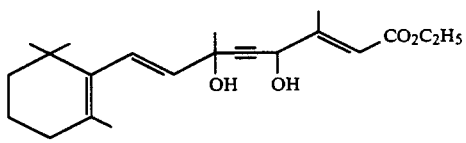

into vitamin A of the formula

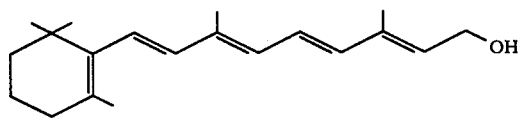

The yield of this reaction would be 70%. In reality, the yield obtained is 20% of vitamin A constituted by several isomers. This result is in accord with a recent work, J. Am. Chem. Soc. 1986, 108, 1338, which shows that, on a similar substrate, the reduction using this hydride leads to 75% of all-trans derivative and 25% of cis isomer.

S. M. Makin, Russian Chem. Revs. 38,237 (1969) and Zhur. Org. Khim. 2,1586 (1966), also describe the reduction of an acetylenic diol into a retinol derivative without any indication of the yield.

The synthesis method explored by A. D. Brock and J. Lugtenburg, Rec. Trav. Chim. Pays-Bas 1980, 363, uses an acetylenic organomagnesium compound and leads to the production of an all-trans, 9-cis and 13-cis mixture. This method then does not permit to attain any stereospecificity.

Finally, among the methods not employing acetylenic compounds, one can mention the works of M. R. Fransten and others, Rec. Trav. Chim. Pays-Bas, 1980,384, which lead to the production of a mixture of all-trans and 11-cis isomers.

One of the objects of the present invention is to provide a synthesis process for a precursor compound of vitamin A, such as an ether, which permits to obtain either the all-trans isomer or the 13-cis isomer of vitamin A, in a stereospecific manner.

Another object of the invention is to provide such a process which permits to produce this derivative in an industrially interesting yield.

These objects as well as others, which will appear below, are achieved by a synthesis process, on the one hand, of all-trans compounds selected from the group consisting of vitamin A and its ethers, retinol and retinoic acid and, on the other hand, of their 13-cis isomers, which is characterized by the fact that one effects a stereospecific reduction of the two hydroxyl groups of an ether-diol precursor of vitamin A by a mixture (titanium trichloride, aluminum lithium hydride), in an anhydrous solvent medium, at a temperature between 5° C. and about 40° C. and that optionally, one converts the resulting ether into vitamin A, retinol or retinoic acid.

The solvent medium is preferably constituted by at least one ether such as diethyl ether, tetrahydrofuran, dioxan and mixtures thereof.

Advantageously, one reduces the ether-diol at a temperature of about 20° C.

Preferably, one reacts 0.8 equivalent of the ether-diol precursor of vitamin A with 2 equivalents of titanium trichloride and 1 equivalent of aluminum lithium hydride.

The mixture of titanium trichloride and aluminum lithium hydride ($TiCl_3/LiAlH_4$) has been used for the first time by McMurry, Acc. Chim. Res, (1974), 7 281, for the reductive coupling of carbonyl compounds into olefins in accordance with the reaction scheme:

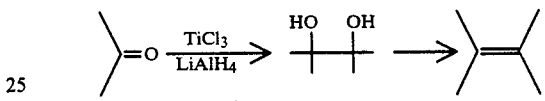

Later, H. M. Walborsky, J. A. Chem. Soc. (1982), 104,5807, used this mixture to prepare 1,3 dienes in accordance with the reaction scheme:

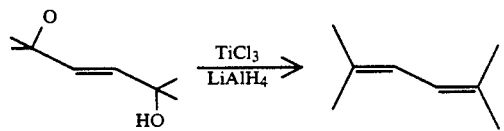

According to the invention, one uses this reaction mixture to reduce diols having unsaturated portions on the one hand and on the other hand hydroxyl groups without modifying the stereochemistry of the molecule, which is quite an unexpected result.

Preferably, the ether-diol precursor of vitamin A is selected from the group consisting of:
the all-trans ether-diol of formula (VII):

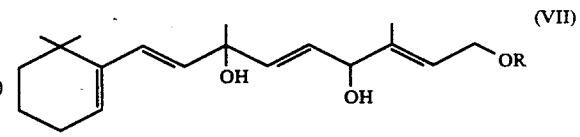

wherein R is a $C_1$–$C_6$ alkyl residue, an aralkyl residue optionally substituted by one or more alkoxy groups, such as 4'-methoxy benzyl and 3',4'-dimethoxy benzyl, or a

residue wherein $R_1$, $R_2$ and $R_3$, identical or different, represent a $C_1$–$C_6$ alkyl residue, linear or branched, or an aryl residue optionally substituted, such as t-butyl-dimethylsilane, t-butyldiphenylsilane or triethylsilane, 10-trans ether-diol of formula (VIII'a)

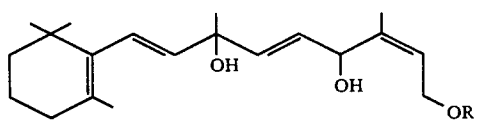

10-cis ether-diol of formula (VIII'b)

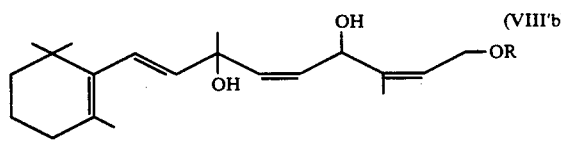

in which formulas R has the meanings indicated above.

According to a first variation of a first embodiment of the invention, one obtains the all-trans ether-diol, precursor of vitamin A, of formula (VII) by etherification of the terminal alcohol function of the compound of formula (VIa):

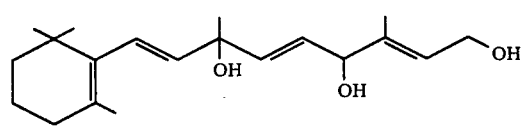

by a $C_{1-6}$ alkyl residue, an aralkyl residue optionally substituted by one or more alkoxy groups, principally 4'-methoxy benzyl and 3',4'-dimethoxy benzyl, or a $$-\underset{\underset{R_3}{|}}{\overset{\overset{R_1}{|}}{Si}}-R_2$$

residue where $R_1$, $R_2$ and $R_3$ have the above indicated meanings, principally t-butyldimethyl silane residue, in the presence of imidazole, at ambient temperature, followed by an extraction with ether. Advantageously, the extraction with ether is followed by washing with a saturated solution of ammonium chloride, drying and evaporation.

Preferably, to obtain the compound of formula (VIa), one reacts an acetylenic ester of ethynyl-β-ionol of formula (V):

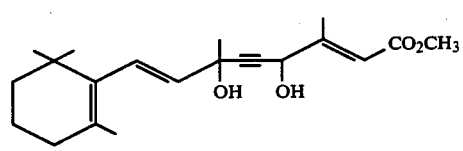

with lithium aluminum hydride; after treatment in dilute acid medium, one extracts the aqueous phase with ether, and one purifies the organic phase, which contains the compound of formula (VIa).

Advantageously, to obtain the compound of formula (V), one reacts the known compound ethynyl-β-ional of formula (III):

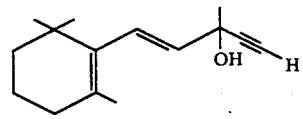

with ethylmagnesium bromide then with methyl γ-oxysenecioate of formula (IV):

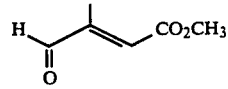

After treatment one extracts with ether the compound of formula (V).

In accordance with a second variation of the first embodiment, one obtains the 10-cis ether-diol, precursor of vitamin A, of formula (VIII'b) by etherification of the terminal alcohol function of the compound of formula (VIb):

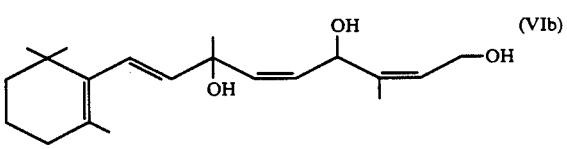

by a $C_1$-$C_6$ alkyl residue, an aralkyl residue optionally substituted by one or more alkoxy groups, principally 4'-methoxy benzyl and 3', 4'-dimethoxy benzyl, or a -$SiR_1R_2R_3$ residue where $R_1$, $R_2$ and $R_3$ have the above-indicated meanings, principally the triethylsilane residue, in the presence of imidazole, at ambient temperature, followed by an extraction with ether.

Preferably, to obtain the compound of formula (VIb), one reduces the compound of formula (VI'):

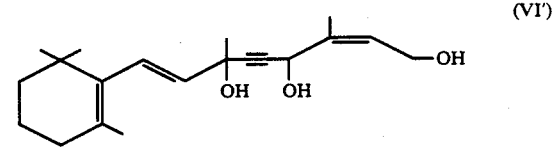

by hydrogen, in the presence of the Lindlar catalyst.

In accordance with a first variation of the second embodiment of the present invention, one obtains the 10-cis ether-diol, precursor of vitamin A, of formula (VIII'b) by hydrogen reduction, in the presence of the Lindlar catalyst, of the compound of formula (VII'):

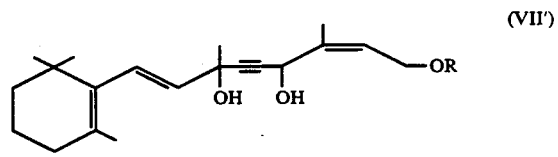

wherein R has the same meanings as those indicated above.

In accordance with a second variation of this second embodiment, one obtains the 10-trans ether-diol, precursor of vitamin A, of formula (VIII'a) by reduction, with lithium aluminum hydride, of the compound of formula (VII') indicated above and extraction with ether of the organic phase containing the compound of formula (VIII'a).

According to this second embodiment, one obtains advantageously the compound of formula (VII') by etherifying the compound of formula (VI')

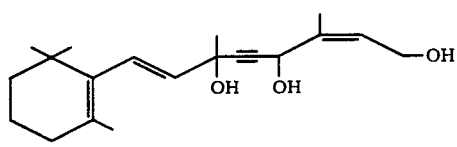

by a $C_1$-$C_6$ alkyl residue, an aralkyl residue optionally substituted by one or more alkoxy groups, principally the residue of 4'-methoxy benzyl or 3', 4'-dimethoxy benzyl, or the

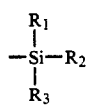

residue where $R_1$, $R_2$ and $R_3$ have the above given meanings, such as the t-butyldiphenylsilane residue, in the presence of imidazole, at ambient temperature, this etherification being followed by an extraction with ether. Preferably, the extraction with ether is followed by a washing with a saturated solution of ammonium chloride, drying and evaporation.

Advantageously, one obtains the compound of formula (VI') by reacting a compound of formula (V')

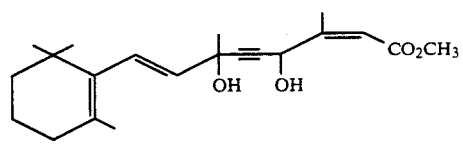

with diisobutyl aluminum hydride, then by effecting an extraction of the organic phase, which contains the compound of formula (VI').

To obtain the compound of formula (V'), one reacts, preferably, the known compound ethynyl-β-ionol of formula (III) with ethylmagnesium bromide, then with a compound of formula (IV')

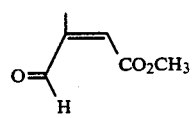

that one prepares by reacting known butenalid of the formula

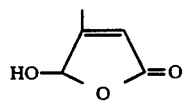

with sodium hydride, then with trimethyl-oxonium fluoroborate.

The process according to the present invention permits to obtain either by the first variation of the first embodiment, an all-trans ether of vitamin A of formula (VIII):

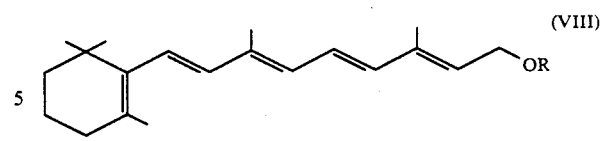

wherein R has the above indicated meanings, or by the second variation of the first embodiment or by one or the other of the two variations of the second embodiment, a 13-cis ether of vitamin A of formula (IX'):

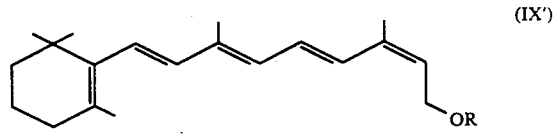

wherein R has the above-indicated meanings.

Starting with these ethers, it is possible to obtain all-trans vitamin A, all-trans retinol, all-trans retinoic acid, as well as their 13-cis isomers.

To better understand the present invention, several non-limiting examples are now given.

EXAMPLE 1

Preparation of the all-trans ether of vitamin A having the formula (VIII)

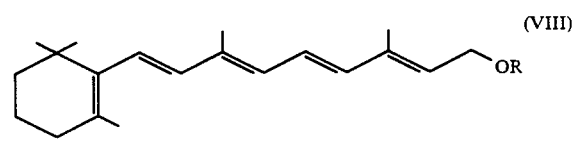

wherein R is

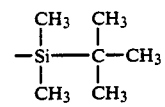

(t-butyl dimethylsilane).

a) Preparation of ethynyl-β-ionol of formula (III)

This known compound is obtained in accordance with the preparatory method described by A. D. Brock and J. Lugtenburg in Rec. Trav. Chim. Pays-Bas, 1980,363:

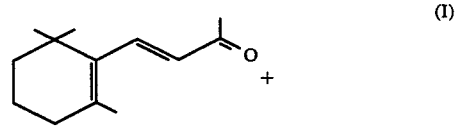

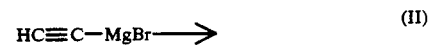

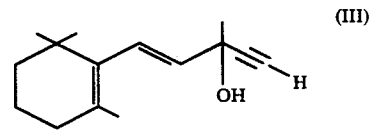

by reacting β-ionone (I) with ethynylmagnesium bromide (II).

The yield of this reaction is about 80%.

(b) Preparation of the acetylenic ethynyl-β-ionol ester (V)

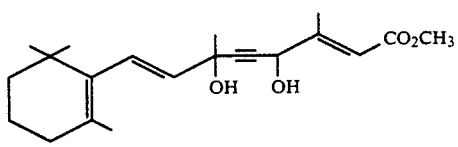

To a solution of 6.54 g (30 mmoles) of ethynyl-β-ionol of formula (III) in 50 ml of anhydrous tetrahydrofuran there is added a solution of ethyl magnesium bromide, prepared starting with 1.75 g of Mg and 7.85 g of ethyl bromide (72 mmoles) in 70 ml of tetrahydrofuran. After having let stand for one hour at ambient temperature, one adds slowly 4.69 g (33 mmoles) of methyl γ-oxo senecioate of formula (IV) in solution in 30 ml of anhydrous tetrahydrofuran; the said compound of formula (IV) has been obtained by the procedure described by K. Sisido and others in J. Am. Chem. Soc. 1960, (82), 2286. After this addition, the solution slowly becomes clear and turns green. The progress of the reaction can be followed by thin layer silica chromatography (eluant: ethylacetate/n-hexane in a volume ratio 30/70, Rf=0.25).

After one hour at ambient temperature, one pours the reaction mixture into 200 ml of a saturated solution of NH$_4$Cl cooled to 0° C.

The product, extracted with ether and dried on sodium sulfate is then purified by chromatography (eluant: ethylacetate/n-hexane in a volume ratio of 30/70).

The yield of the acetylenic ester of ethynyl-β-ionol (V), isolated after chromatography, is about 80%.

Analysis by nuclear magnetic resonance (200 MHz, CDCl$_3$) gave the following results: δ: 0.98 (s, 6H, CH$_3$ in 1); 1.42–1.64 (m, 4H, CH$_2$ in 2 and 3); 1.60 (s, 3H, CH$_3$ in 9); 1.66 (s, 3H, CH$_3$ in 5); 1.98 (t, 2H, CH$_2$ in 4, J=6 Hz); 2.24 (s, 3H, CH$_3$ in 13); 3.72 (s, 3H, OCH$_3$); 4.89 (s large, 1H, H in 12); 5.95 (AB, 2H, J=16 Hz, Δν159 Hz, H in 7 and 8); 6,12 (s large, 1H, H in 14).

(c) Preparation of the triol of formula (VIa)

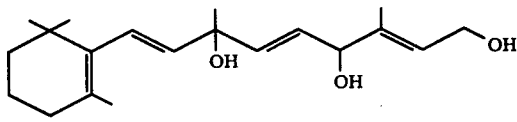

To a solution of 1.5 g of the acetylenic ester of formula (V) obtained in the preceding step in 40 ml of anhydrous tetrahydrofuran at −20° C. there are added 2 determined equivalents of LiAlH$_4$ (330 mg). After the addition, the mixture is heated at 30° C. for 2 hours. There are then added a few drops of ethyl acetate and then a few drops of water and finally 40 ml of a 5 weight percent aqueous solution of HCl.

The phases are separated and the aqueous phase extracted with ether (4×20 ml). The organic phases are then washed with 50 ml of water saturated with NaCl and dried on MgSO$_4$.

The product is then purified by chromatography (eluant: ethylacetate/n-hexane in a volume ratio of 80/20; Rf=0.2). The yield of isolated product (VIa) is about 80%.

The product is a colorless oil whose nuclear magnetic resonance analysis (200 MHz, CDCl$_3$) gave the following results: δ:0.97 (s, 6H,CH$_3$ in 1); 1.43 (S, 3H,CH$_3$ in 9); 1.46–1.63 (m, 4H,CH$_2$ in 2 and 3); 1.65 (s, 6H,CH$_3$ in 5 and 13); 1.89–2.00 (m, CH$_2$ in 4); 4.20 (d, 2H, J=7 Hz,CH$_2$ in 15); 4.56 (d, 1H, J=6 Hz, H in 12); 5.79 (AB, 2H, J=16 Hz, Δν=107 Hz,H$_7$ and H$_8$); 5.65–5.94 (system with 12 lines, 3H,H$_{10}$,H$_{11}$, H$_{14}$).

(d) Preparation of the ether-diol of formula (VII), precursor of vitamin A

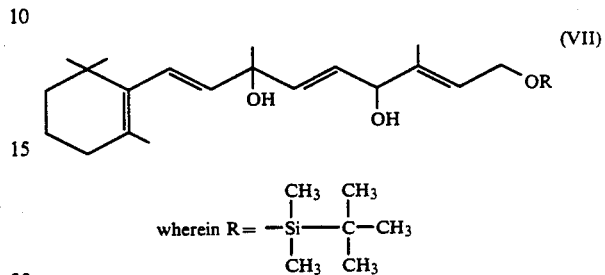

To 1.20 g of the triol of formula (VIa) in 50 ml of dimethylformamide, there are added one equivalent of t-butyldimethyl silane (0.57 g) and 2 equivalents of imidazole (0.51 g). The solution is stirred for 6 hours at ambient temperature and diluted with 500 ml of water. The product is extracted with ether (3×40 ml). The ether phases are washed with a saturated solution of NH$_4$Cl (3×40 ml). After drying on MgSO$_4$ and evaporation of the solvent, one obtains 1.65 g (quantitative yield) of a yellow oil usable without another purification in the following step.

The yield of isolated product (VII) is about 80% and analysis by nuclear magnetic resonance (200 MHz, CDCl$_3$) gave a spectrum superimposable on that of the starting triol with two supplementary peaks: δ:0.11 (s, 6H,2CH$_3$); 0.90 (s, 9H,t.Bu).

(e) Preparation of the all-trans ether of vitamin A of formula (VIII)

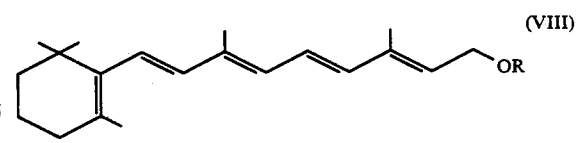

wherein R=t-butyldimethylsilane

The preparation of Ti° titanium, described by Walborsky (H. M. Walborsky, H. M. Wüst, J. Am. Chem. Soc. 1982, 104,5807) has been modified by using determined LiAlH$_4$. Two equivalents of TiCl$_3$ (1.43$_q$) are weighed in a flask previously ovendried. One adds 30 ml of anhydrous tetrahydrofuran and one equivalent of LiAlH$_4$ determined in ether (0.176$_q$) under argon.

The mixture is stirred for 10 minutes at ambient temperature and one then adds 0.8 equivalent (1.61$_g$) of the diol of formula (VII) obtained in the preceding steps in solution in 20 ml of tetrahydrofuran. After having let stand for one hour at ambient temperature, the medium is hydrolyzed by 10 ml of water and 60 ml of decinormal HCl.

The phases are separated and the aqueous phase extracted with ether (2×30 ml). The organic phases are then washed with 60 ml of a saturated solution of NaCl, then dried on MgSo$_4$ and evaporated.

One thus obtains 1.30 g of a yellow oil, in a yield of about 85%, usable directly. Analysis by nuclear magnetic resonance (200 MHz, CDCl₃) gave a spectrum superimposable on that of commercial vitamin A with two supplemental peaks: δ:0.11 (s,6H,2CH₃); 0.90 (s,9H T.Bu)

EXAMPLE 2

Preparation of the 13-cis ester of vitamin A of Formula (IX')

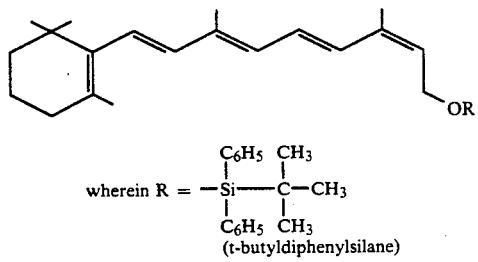

wherein R = 
$$\text{—Si}\begin{matrix}C_6H_5\\|\\|\\C_6H_5\end{matrix}\text{—C}\begin{matrix}CH_3\\|\\|\\CH_3\end{matrix}\text{—CH}_3$$
(t-butyldiphenylsilane)

(a) Preparation of the compound of formula (V'):

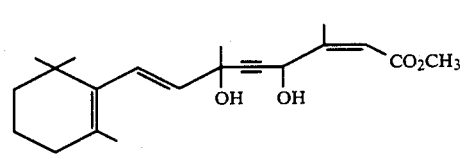

One dissolves 1 g of butanolide, prepared according to C. G. Wesmuth, J. Org. Chem. 1981, (46), 4889, in 25 cm³ of anhydrous tetrahydrofuran. One cautiously adds 0.210 g of NaH prepared starting with commercial sodium hydride by vigorous stirring in anhydrous hexane under argon for 30 minutes then filtering the suspension thus obtained, double rinsing with anhydrous pentane and prolonged drying in a vacuum. The reaction mixture is then cooled to −78° C. and stirred for one hour. One adds 1.7 g of trimethyloxonium fluoroborate and permits the temperature to rise slowly. The reaction mixture is poured on 50 cm³ of a saturated solution of ammonium chloride. The aqueous phase is extracted with 25 cm³ of ether. The organic phases are combined, washed with a saturated solution of sodium chloride (2×50 cm³), dried on sodium sulfate and evaporated. One thus obtains 1.2 g of a pure colorless liquid corresponding to the compound of formula (IV'), in a yield in the order of 95%. The reaction scheme was the following:

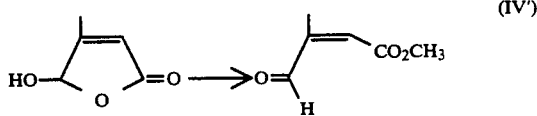

One then repeats the operating method of step (b) of Example 1 by replacing the compound of formula (IV) by the compound of formula (IV') obtained as indicated. The progress of the reaction can be followed by thin layer silica chromatography (eluant: ethylacetate/hexane in a volume ratio 30/70; Rf=0.25). The yield of this reaction of compound (V') is about 100%.

Analysis by nuclear magnetic resonance (200 MHz, CDCl₃) gave the following results: δ:0.98(s,6H,CH₃ in 1); 1.42–1.66(m,4H,CH₂ in 2 and 3); 1.66(s,3H,CH₃ in 9); 1.98(t badly resolved, 2H,CH₂ in 4, J=6 Hz); 2,10(s,3H,CH₃ in 5); 2,24(s,3H,CH₃ in 13); 4.89(s,1H,H₁₂); 5.55(d,1H,H₈, J=16 Hz); 6.00 and 6.12(2s,H₁₄ corresponding to the 2 C₁₂-C₉ diastereoisomers); 6.35(d,1H,H₇, J=16 Hz).

(b) Preparation of the compound of formula (VI')

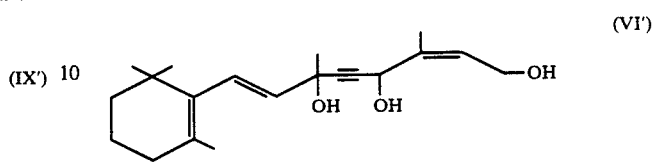

One dissolves 6 g of compound (V') in 250 cm³ of anhydrous tolvene, under argon. One adds, at 0° C., 50 cm³ of a 1M solution of diisobutylaluminum hydride.

The progress of the reaction can be followed by thin layer silica chromatography (eluant: ethylacetate/n-hexane in a volume ratio 70/30; Rf=0.30); after 15 minutes, the reaction is completed.

One then adds 20 cm³ of methanol, then a 5 weight percent HCl aqueous solution until an acid pH. The organic phase is separated and the aqueous phase is extracted twice with 100 cm³ of water, then two times with 100 cm³ of a saturated solution of sodium chloride.

After drying on magnesium sulfate and evaporation of the solvent, one obtains an oil which will be used without other purification in the following step and which corresponds to the compound of formula (VI').

(c) Preparation of the compound of formula (VII'):

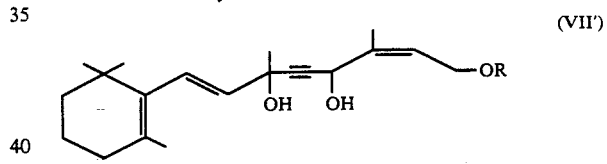

wherein R=t-butyldiphenylsilane.

The operating method is identical to that described in step (d) of Example 1 but by using as the starting material the compound of formula (VI') obtained in the preceding step and by replacing the t-butyldimethylsilane chloride with t-butyldiphenylsilane chloride. The compound of formula (VII') obtained is purified by silica gel chromatography (eluant: ethylacetate/n-hexane in a volume ratio 20/80).

The yield of compound (VII') is of the order of 85% and analysis by nuclear magnetic resonance (200 MHz, CDCl₃) gave the following results: δ:0.99 (s,6H,CH₃ in 1); 1.05(s,9H,t-Bu); 1.42–1.64(m,4H,CCH₂ in 2 and 3); 1.59,1.61,1.67(3s, 3×3H, CH₃ in 5.9 and 13); 1.98(t,2H,CH₂ in 4, J=6 Hz); 4.28(d,2H,CH₂ in 15, J=6 Hz); 4.79(d,1H,H₁₂, J=5 Hz); 5.56(d,1H,H₈; J=16 Hz); 5.82(t,1H,H₁₄ J=6 Hz); 6.37(d,1H,H₇, J=16 Hz); 7.36–7.45 and 7.66–7.71(10H, H aromatics).

(d) Preparation of the compounds of formula VIII'a) and VIII'b)

Starting with the compound of formula (VII') obtained above, one can obtain either the 10-trans isomer of formula (VIII'a), or the 10-cis isomer of formula (VIII'b).

(1) The 10-trans isomer of formula (VIII'a):

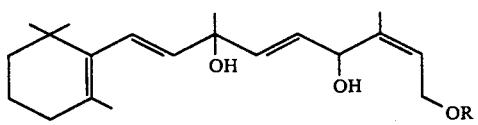

wherein R = T-butyldiphenylsilane.

One dissolves 2 g of the compound of formula (VII') in 100 cm³a of anhydrous ether under argon at 0° C. One adds 1.2 equivalents of a standard solution of LiAlH₄ in ether. After letting it stand for one hour at 0° C., one pours the mixture over 80 cm³ of a saturated solution of ammonium chloride, then one dilutes with 50 cm³ of water. After separation of the organic phase, the aqueous phase is extracted twice with 50 cm³ of ether. The organic phases are combined and washed with 100 cm³ of a saturated solution of sodium chloride, then dried on magnesium sulfate and evaporated. One obtains an oil which is purified by silica gel chromatography (eluant: ethylacetate/n-hexane in a volume ratio 30/70).

The yield of this reaction is of the order of 65%, and analysis by nuclear magnetic resonance (200 MHz, CDCl₃) gave the following results: δ:0.97(s,6H,CH₃ in 1); 1.04(s,9H,t-Bu); 1.41,1.64(2s,6H,CH₃ in 5 and 13); 1.42(s,3H,CH₃ in 9); 1.45–1.61(m,4H,CH₂ in 2 and 3); 1.96(t,2H,CH₂ in 4, J=6 Hz); 4.27(d,2H,CH₂ in 15, J=6 Hz); 4.50(d,1H, H₁₂, J=6 Hz); 5.52(d,1H,H₈, J=16 Hz); 5.68(t,1H,H₁₄, J=6 Hz); 5.77(AB,2H,H₁₀ and H₁₁, J$_{ab}$=16 Hz, Δν=4OH₃, H₁₁ resolved by J=6 Hz); 6.07(d,1H,H₇, J=16 Hz); 7.34–7.43 and 7.66–7.71 (m,10H aromatics).

(2) 10-cis isomer of formula (VIII'b)''

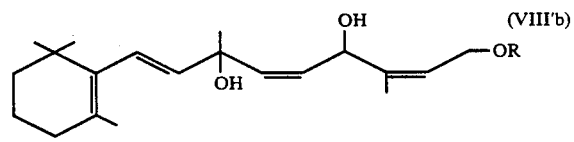

where R is the t-butyldiphenylsilane radical 100 mg of the compound (VII') are dissolved in 5 ml of absolute methanol. After addition of 200 mg of Lindar catalyst (Pd/CaCO₃ deactivated with Pb), the air contained in the reactor is removed under a vacuum and replaced by hydrogen. The suspension is then stirred vigorously for 72 hours and the reaction followed by thin layer chromatography (eluant: ethylacetate/n-hexane in a volume ratio 80/20; Rf of starting product=0.21; Rf of diastereoisomer products=0.26 and 0.32). The catalyst is filtered and the solvent evaporated. The two diastereoisomers were separated by chromatography for identification.

The yield of this reaction is about 80% and analysis by nuclear magnetic resonance (200 MHz, CDCl₃) gave the following results: Diastereoisomer Rf=0.26: δ:0.99(s,6H,CH₃ in 1); 1.05(s,9H,t-Bu); 1.48(s,6H) and 1.67(s,3H) (CH₃ in 5, 9 and 13); 1.43–1.65(m,4H,CH₂ in 2 and 3); 1.98(t,2H,CH₂ in 4, J=6 Hz); 2.93(m,2H,OH); 4.27(d,2H,CH₂ in 15, J=6 Hz); 5.06(d,1H,H₁₂, J=7 Hz); 5.58(AB,2H,H₁₀ and H₁₁, J=12 Hz, Δν=46.5H₃,H₁₁ resolved by J=7 Hz); 5.70(t,1H,H₁₄, 6 Hz); 5.87(AB,2H,H₇ and H₈, J=16 Hz, Δν=105 Hz); 7.34–7.44 and 7.67–7.72(m,10H aromatics). Diastereoisomer Rf=0.32: δ:0.99(s,6H,CH₃ in 1); 1.05(s,9H,T-Bu); 1.42–1.67(m,4H,CH₂ in 2 and 3); 1.47(s,3H,CH₃ in 9); 1.49(s,3H,CH₃ in 5); 1.66(s,3H,CH₃ in 13); 1.98(t,2H,CH₂ in 4, J=6 Hz); 2.8(m,2H,OH); 4.28(d,2HCH₂ in 15, J=6 Hz); 5.11(d,1H,H₁₂, J=6 Hz); 5.54(AB,2H,H₁₀ and H₁₁, J=12.5 Hz, Δν=48.5 Hz, H₁₁ resolved by J=6 Hz); 5.671(d,1H,H₈, J=16 Hz); 5.71(t,1H,H₁₄, J=6 Hz); 6.10(d,1H,H₇, J=16 Hz); 7.34–7.47 and 7.64–7.72(m,10H aromatics).

(e) Preparation of the 13-cis ether of vitamin A of formula (IX')

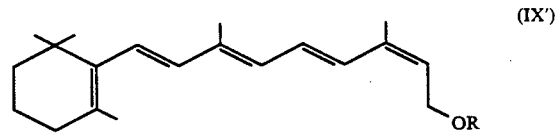

wherein R is the t-butyldiphenylsilane radical

One uses the operating method described in step (e) of example 1. The compound of formula (VII) is replaced by the compound of formula (VIII'a) or (VIII'b) (10-cis or 10-trans). The yield is in the order of 100%.

Analysis by nuclear magnetic resonance (200 MH₃, CDCl₃) gave the following results: δ:1.04(s,6H,CH₃ in 1); 1.06(s,9H,t-butyl); 1.43–1.64 (m,4H,CH₂ in 2 and 3); 1.65,1.73,1.96(3s,3×3H, CH₃ in 5,9,13); 2.03(t,2H,CH₂ in 4, J=6 Hz); 4.38(d,2H,CH₂ in 15, J=6 Hz); 5.71(t,1H,H₁₄, J=6 Hz); 6.11(d,1H,H₁₀, J=11 Hz); 6.14(s,2H,H₇ and H₈); 6.29 (d,1H,H₁₂, J=15 Hz); 6.55(dd,1H,H₁₁, J=15 and 11 Hz); 7.34–7.45(m,6H aromatics); 7.65-7.74(m,4H aromatics).

In the two examples above, the determining step is the stereospecific reduction by a LiAlH₄/TiCl₃ mixture of compounds (VII), (VIII'a) or (VIII'b) into ethers of vitamin A respectively alltrans of formula (VIII) or 13-cis of formula (IX'). This reduction is accomplished with a yield of 100%.

One notes that one uses, in these two examples, standard solutions of lithium aluminum hydride and that the reactions of steps (e) of Examples 1 and 2 are carried out at ambient temperature and not at reflux.

EXAMPLE 3

Preparation of the 13-cis ether of vitamin A of formula (IX'')

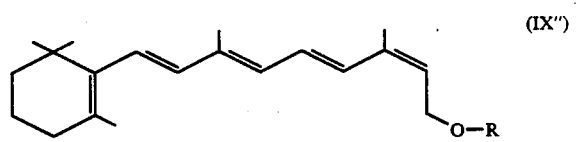

wherein R represents the triethylsilane radical (a) Preparation of the compound of formula (VIb):

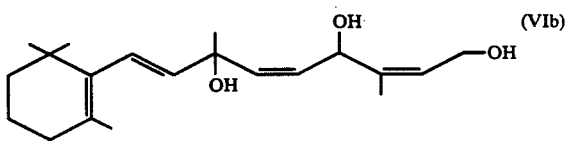

One dissolves 1 g of compound (VI') obtained at the end of step (b) of Example 2 in 10 cm³ of methanol. One adds a catalytic amount of the Lindlai Catalyst. One stirs at ambient temperature for 16 hours under a hydrogen atmosphere at atmospheric pressure. After filtration of the catalyst and distillation of the solvent under reduced pressure, one recovers 1 g of colorless oil (compound of formula VIb), which is used without additional purification in the following preparation.

(b) Preparation of the compound of formula (VIII'b)

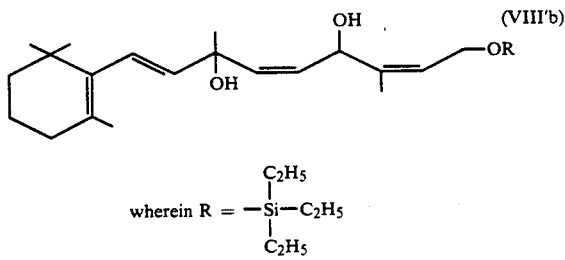

The operating procedure is analogous to that of step (d) of Example 1, the chlorodimethyltert.butyl silane being, however, replaced by chlorotriethylsilane. The yield of this reaction is 90%. Compound (VIII'b) is employed without further purification in the following steps.

(c) Preparation of the compound of formula (IX'')

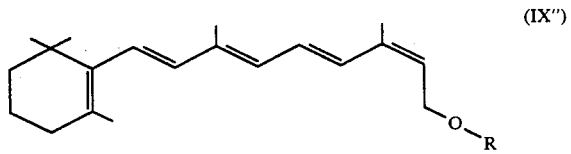

wherein R has the same meaning as in the preceding step.

The method of operation is identical to that of step (e) of Example 1.

The reaction is followed by thin layer silica chromatography. When the starting product has disappeared, the reaction mixture is rapidly filtered on silica gel and the solvent is distilled under reduced pressure. Compound (IX'') is obtained in a quantitative yield. It is employed without further purification in the following steps.

EXAMPLE 4

Preparation of 13-cis retinol of formula (X'')

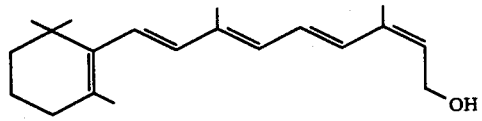

- 1 g of the compound of formula (IX'') obtained in Example 3 is dissolved in 15 cm³ of a mixture (tetrahydrofuran-acetonitrile) containing ⅛ of tetrahydrofuran. The solution thus obtained is treated with 5 equivalents of anhydrous sodium fluoride and 0.1 equivalent pure pyridinium fluoride, preferably dry and crushed into fine particles just before use. The reaction is carried out in the absence of light, under argon, after having added to the solution 2 g of a dehydrating agent constituted by a "molecular sieve" of 4A.

After 5 hours of stirring at ambient temperature, the reaction mixture is treated with 10 cm³ of a saturated solution of ammonium chloride and 10 cm³ of water. After decanting, the aqueous phase is extracted twice with 10 cm³ of ether. The organic phases are combined and washed with 20 cm³ of a saturated solution of sodium chloride. After drying on sodium sulfate, the solvent is distilled at ambient temperature under reduced pressure.

The yield of this reaction is greater than 80%. One obtains 1 g of a bright yellow oil giving a single spot in thin layer silica gel chromatography (eluant: ether/hexane in a volume ration 10/90 Rf=0.10).

Analysis of the resulting product by nuclear magnetic resonance (200 MHz, CDCl₃) gave a spectrum identical to that described by R. S. H. Lin and A. E. Asato, Tetrahedron, 40(11), 1931(1984), for 13-cis retinol.

EXAMPLE 5

Preparation of 13-cis retinol of formula (XI'')

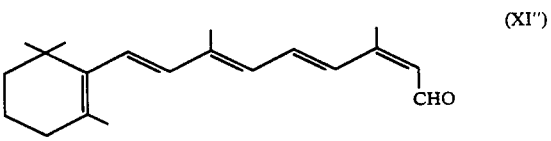

One dissolves 1 g of 13-cis retinol obtained in Example 4 in 15 cm³ of anhydrous carbon tetrachloride in the absence of light. One adds, under vigorous stirring, 1.5 g (5 equivalents) of freshly prepared MnO₂. After 30 minutes at ambient temperature, the suspension is rapidly filtered on silica gel and the solvent is distilled at ambient temperature under reduced pressure.

One thus obtains 1 g of 13-cis retinol giving a single spot in thin layer silica gel chromatography (eluant: ether/hexane in a volume ratio 10/90; Rf=0.25).

Analysis by nuclear magnetic resonance (200 MHz, CDCl₃) gave a spectrum identical to that described by R. S. H. Lin and A. E. Asato, Tetrahedron, 40 (II), 1931 (1984) for 13-cis retinol.

EXAMPLE 6

Preparation of 13-cis retinoic acid of formula (XII'')

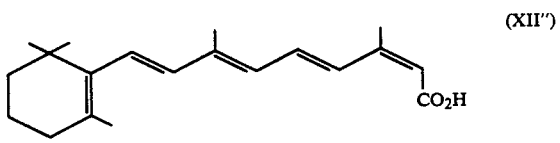

(a) Preparation of the ethyl ester of 13-cis retinoic acid

One dissolves 1 g of crude 13-cis retinol obtained in Example 5 in 15 cm³ of ethanol. One adds successively 5 equivalents of sodium cyanide (0.86 g) and 6 equivalents of AgO(2.6 g). The suspension thus obtained is stirred at 40° C. in the absence of light for 14 hours. The reaction mixture is filtered and the solution is chromatographed on silica gel (eluant: ethylacetate/hexane in a volume ratio 2/98). One thus obtains 0.65 g of the ethyl ester of 13-cis retinoic acid; the yield is about 60%.

Analysis by nuclear magnetic resonance (200 MHz, CDCl₃) gave a spectrum identical to that described by R. S. H. Liu and A. E. Asato, Tetrahedron, 40 (II), 19131 (1984) for the methyl ether of 13-cis retinoic acid with the exception the characteristics signal of the methyl group.

(b) Hydrolysis

One suspends 0.100 g of the ester obtained above in 5 cm³ of ethanol and 5 cm³ of a 6 m aqueous solution of soda. One stirs at 50° C. in the absence of light until all the solid has dissolved.

The reaction mixture is then diluted with 100 cm³ of water and the ethanol is distilled under reduced pressure. The aqueous phase is acidified up to pH 2 by the addition of HCl in a 10% aqueous solution. One extracts three times with 10 cm³ of ether. One dries on sodium sulfate and distills the solvent under reduced pressure. One recovers a bright yellow solid which is recrystallized in methanol. One thus obtains 13-cis retinoic acid with a yield of 95%.

Analysis by nuclear magnetic resonance (200 MHz, CDCl₃) gave a spectrum identical to that described by R. S. H. Liu and A. E. Asato, Tetrahedron, 40[(II), 1931(1984) for the methyl ester of 13-cis retinoic acid, with the exception of the characteristic signal of the methyl residue.

One has analyzed this 13-cis retinoic acid by chromatography using a Lichrosorb RP(5$^\mu$) column, sold by Merck, of which the height is 25 cm and the diameter, 0.4 cm. The eluant is a mixture consisting of 25 volume percent of a 0.2 volume percent aqueous solution of acetic acid and a 75 volume percent of a 0.2 volume percent solution of acetic acid in methanol. The flow rate is regulated at 1 ml/min. The retention time is 19 minutes.

The resulting chromatogram is superimposable on that of a commercial sample of 13-cis retinoic acid.

EXAMPLE 7

Preparation of all-trans vitamin A of formula (IX)

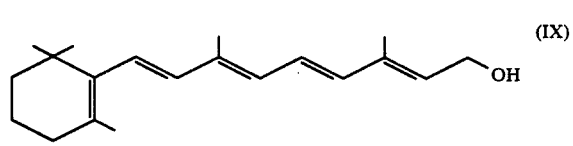

Starting with the all-trans ether of vitamin A of formula (VIII) obtained at the end of step (e) of Example 1, one can obtain stereospecifically pure, all-trans vitamin A.

To 1 equivalent of the silyled ether of vitamin A previously obtained (1.25 g) in solution in 20 ml of tetrahydrofuran, one adds 1.5 equivalents of tetrabutylammonium fluoride. The mixture is stirred for 2 hours at ambient temperature.

The reaction mixture is then filtered on silica, then the silica is washed with ether (2×20 ml). After having evaporated the solvent, the product is chromatographed (eluant: ethyl acetate/n-hexane in a volume ratio 20/80; Rf=0.20).

One thus obtains 740 mg of vitamin A in the form of a yellow solid, at a yield of about 80%, the analysis of which by nuclear magnetic resonance (200 MH₃, CDCl₃) gave a spectrum superimposable on that of commercial vitamin A: $\delta$:1.02 (s, 6H, CH₃ in 1); 1.36–1.68(m, 4H, CH₂ in 2 and in 3); 1.71(s, 3H, CH₃ in 5); 1.87(s, 3H, CH₃ in 9); 2.02(t, 2H, J=6 Hz, CH₂ in 4); 4.31(d, 2H, J=7 Hz, CH₂ in 15); 5.69(t, 1H, H₁₄, J=7 Hz); 6.10(d, 1H, H₁₀, J=11 Hz); 6.13 and 6.14(2 s, 2H, H₇ and H₈); 6.28(d, 1H, H₁₂, J=16 Hz); 6.62(dd, 1H, J=11 Hz and J=16 Hz, H₁₁).

EXAMPLE 8

Preparation of all-trans retinol of formula (X)

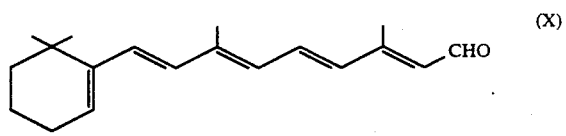

To 1 gram of all-trans vitamin A of formula (IX) obtained in Example 7, dissolved in 15 ml of CH₂Cl₂, one adds 1.5 g (5 equivalents) of MnO2 prepared in accordance with the process described by J. Attenburrow, A. F. B. Cameron, J. K. Chapman, R. M. Evans, B. A. Hans, A. B. A. Janssen and T. Walker in J. Chem. Soc. 1952, 1094.

The suspension is stirred in the absence of light for 2 hours. The reaction is quantitative. The mineral compounds are removed by filtration. After evaporation of the solvent, there remains 1 gram of a pure bright yellow solid of formula (X).

Analysis by nuclear magnetic resonance (200 MHz, CDCl₃) gave the following results: $\delta$:1.04 (s, 6H, CH₃ in 1); 1.45–1.70(m, 4H, CH₂ in 2 and 3); 1.73(s, 3H, CH₃ in 5); 2.00–2.03(large signal, 5H, CH₂ in 4 and CH₃ in 9); 2.33(s, 3H, CH₃ in 13); 5.98(d, 1H, H₁₄, J=8.0 Hz); 6.20(d, 1H, H₁₀, J=12.0 Hz); 6.27(AB, 2H, H₇ and H₈, J=16.5 Hz, $\Delta\nu$=36 Hz); 6.37(d, 1H, H₁₂, J=15.4 Hz); 7.15(dd, 1H, H₁₁, J=15.4 and 12.0 Hz); 10.12(d, 1H, H₁₅, J=8.0 Hz).

EXAMPLE 9

Preparation of all-trans retinoic acid of formula (XI)

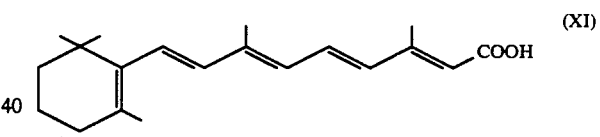

(a) One prepares from the very first silver oxide AgO by the process of F. Jirsa (Z. Anorg. Allgem. Chim. 1935, 225, 302) by adding to 7 g of silver nitrate dissolved in 25 g of water a solution of 15 g (2 equivalents) of KMnO₄ in 300 ml of water, then 15 g (6 equivalents) of KOH dissolved in 75 ml of water. The resulting suspension is stirred for 2 hours at ambient temperature, then filtered. The residue is washed with water until the wash waters are colorless. One thus obtains a black solid, which is stored at 40° C. for 2 hours. The composition of the product thus obtained is about 60% AgO and 40% Ag₂O.

(b) One then proceeds to an oxidation of retinol in accordance with the process of preparation described by E. J. Corey, N. W. Gilman, B. E. Garnem, J. Am. Chem. Soc., 90, (1968), 5616.

One dissolves 200 mg of the retinol of Example 8 in 20 ml of methanol containing 0.05 weight percent of water and one adds 1.4 g (15 equivalents) of silver oxide AgO previously prepared and 180 mg (5 equivalents) of NaCN. The suspension is kept stirred for 18 hours in the absence of light.

The insoluble salts are then removed by filtration on silica and one submits the product to chromatography (eluant: ethylacetate/n-hexane in a volume ratio 30/70; Rf of the retinol=0.70; Rf of retinoic acid=0.25).

The yield of all-trans retinoic acid is about 60% and analysis by nuclear magnetic resonance (200 MHz, CDCl3) gave the following results: δ:1.03(s, 6H, CH3 in 1); 1.44–1.62(m, 4H, CH2 in 2 and 3); 1.72(s, 3H, CH2 in 5); 2.01–2.06(large peak, 5H, CH3 in 9 and CH2 in 4); 2.37(s, 3H, CH3 in 13); 5.80(s, 1H, H14); 6.14(d, 1H, J=16 Hz, H8); 6.15(d, 1H, H10, J=11 Hz); 6.31(d, 1H, H12, J=15 Hz); 7.05(dd, 1H, H11, J=11 and 15 Hz).

This spectrum is superimposable on that of commercial all-trans retinoic acid.

One has also analyzed this all-trans retinoic acid by chromatography using a Lichrosorb RR (5μ) column, sold by Merck, of which the height is 25 cm and the diameter, 0.4 cm. The eluant is a mixture consisting of 25 volume percent of a 0.2 volume percent aqueous solution of acetic acid and 75 volume percent of a 0.2 volume percent acetic acid solution in methanol. The flow rate is regulated at 1 ml/min. The retention time is about 100 minutes.

The resulting chromatogram is superimposable on that of a commercial sample of all-trans retinoic acid.

What is claimed is:

1. A process for the synthesis of an all-trans compound selected from the group consisting of vitamin A and its ethers, retinol and retinoic acid, and their 13-cis isomers comprising effecting stereospecific reduction of the two hydroxyl groups of an ether-diol, precursor of vitamin A with a mixture of 2 equivalents of titanium chloride and 1 equivalent of lithium aluminum hydride in an anhydrous solvent medium at a temperature between 5° C. and about 40° C. and optionally converting the resulting ether into vitamin A, retinol or retinoic acid.

2. The process of claim 1 wherein 0.8 equivalent of said ether-diol is reacted.

3. The process of claim 1 wherein the said stereospecific reduction of said ether-diol is carried out at a temperature near 20° C.

4. The process of claim 1 wherein said anhydrous solvent medium is diethyl ether.

5. The process of claim 1 wherein said ether-diol is selected from the group consisting of
(i) all-trans ether-diol of the formula (VII):

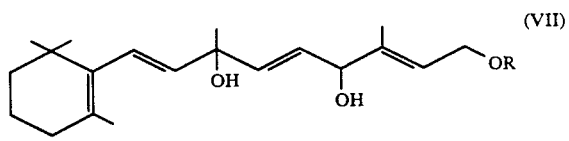

wherein
R is a $C_1-C_6$ alkyl, 4'-methoxy benzyl, 3',4'-dimethoxybenzyl or

wherein $R_1$, $R_2$ and $R_3$, each independently, represent linear or branched $C_1-C_6$ alkyl or phenyl,
(ii) the 10-trans ether-diol of formula (VIII'a)

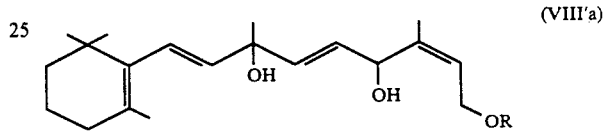

wherein R has the meaning given above, and
(iii) the 10-cis ether diol of formula (VIII'b)

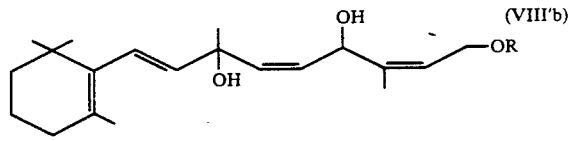

wherein R has the meaning given above.

* * * * *